(12) United States Patent
Moenning, Jr.

(10) Patent No.: US 10,188,814 B2
(45) Date of Patent: Jan. 29, 2019

(54) COMBINATION ANESTHESIA AND SCAVENGER SURGICAL MASK

(71) Applicant: John E. Moenning, Jr., Noblesville, IN (US)

(72) Inventor: John E. Moenning, Jr., Noblesville, IN (US)

( * ) Notice: Subject to any disclaimer, the term of this patent is extended or adjusted under 35 U.S.C. 154(b) by 93 days.

(21) Appl. No.: 14/032,624

(22) Filed: Sep. 20, 2013

(65) Prior Publication Data

US 2014/0083425 A1 Mar. 27, 2014

Related U.S. Application Data

(63) Continuation of application No. 12/540,082, filed on Aug. 12, 2009, now Pat. No. 8,539,953, which is a continuation-in-part of application No. 12/273,748, filed on Nov. 19, 2008, now Pat. No. 8,291,905.

(51) Int. Cl.
| | |
|---|---|
| *A61M 16/06* | (2006.01) |
| *A61M 16/00* | (2006.01) |
| *A61M 16/12* | (2006.01) |
| *A61M 16/08* | (2006.01) |
| *A61M 16/10* | (2006.01) |

(52) U.S. Cl.
CPC .......... *A61M 16/009* (2013.01); *A61M 16/06* (2013.01); *A61M 16/0816* (2013.01); *A61M 16/104* (2013.01); *A61M 16/12* (2013.01); *A61M 16/0875* (2013.01); *A61M 16/107* (2014.02); *A61M 16/1055* (2013.01); *A61M 16/1065* (2014.02)

(58) Field of Classification Search
CPC ............ A61M 16/06–16/0694; A61M 16/638; A61M 16/0891; A61M 2016/0661; A62B 18/00; A62B 18/02; A62B 18/04; A62B 18/06; A62B 18/08–18/088; A62B 7/00; A62B 7/14
See application file for complete search history.

(56) References Cited

U.S. PATENT DOCUMENTS

| | | |
|---|---|---|
| 1,044,031 A | 11/1912 | Drager |
| 2,868,198 A | 1/1959 | Brooke |
| 3,747,599 A | 7/1973 | Malmin |
| 4,015,598 A * | 4/1977 | Brown ................ A61M 16/009 128/205.25 |
| 4,248,218 A | 2/1981 | Fischer |

(Continued)

FOREIGN PATENT DOCUMENTS

| | | |
|---|---|---|
| DE | 33 31 374 A1 | 3/1985 |
| WO | 80/01044 A1 | 5/1980 |

(Continued)

OTHER PUBLICATIONS

International Search Report for International Patent Publication No. PCT/US2009/064713, dated May 6, 2010, 12 pages.

(Continued)

*Primary Examiner* — (Jackie) Tan-Uyen T Ho
*Assistant Examiner* — Ned T Heffner
(74) *Attorney, Agent, or Firm* — Barnes & Thornburg LLP

(57) ABSTRACT

A surgical mask for administering and/or scavenging medical gases includes a nasal mask and an oral mask that envelops the nasal mask. The nasal mask is secured to the oral mask and may be removable from it.

19 Claims, 10 Drawing Sheets

(56) References Cited

U.S. PATENT DOCUMENTS

| | | | |
|---|---|---|---|
| 4,265,239 | A | 5/1981 | Fischer, Jr. et al. |
| 4,770,169 | A | 9/1988 | Schmoegner et al. |
| 4,794,921 | A * | 1/1989 | Lindkvist ............ 128/203.29 |
| 4,807,617 | A | 2/1989 | Nesti |
| 4,895,172 | A | 1/1990 | Lindkvist |
| 4,945,906 | A | 8/1990 | Lindkvist |
| 4,949,714 | A | 8/1990 | Orr |
| 5,005,571 | A | 4/1991 | Dietz |
| 5,018,519 | A | 5/1991 | Brown |
| 5,233,975 | A | 8/1993 | Choate |
| 5,311,862 | A | 5/1994 | Blasdell et al. |
| 5,322,059 | A | 6/1994 | Walther |
| 5,370,110 | A | 12/1994 | Corn |
| 5,400,781 | A | 3/1995 | Davenport |
| 5,419,317 | A | 5/1995 | Blasdell et al. |
| 5,474,060 | A | 12/1995 | Evans |
| 5,513,632 | A | 5/1996 | Nepon et al. |
| 5,676,133 | A | 10/1997 | Hickle et al. |
| 5,715,813 | A | 2/1998 | Guevrekian |
| 5,871,011 | A | 2/1999 | Howell et al. |
| 6,076,524 | A | 6/2000 | Corn |
| 6,237,596 | B1 | 5/2001 | Bohmfalk |
| 6,263,874 | B1 | 7/2001 | LeDez et al. |
| 6,357,437 | B1 | 3/2002 | Jacques |
| 6,698,427 | B1 | 3/2004 | Clowers |
| 6,736,140 | B1 | 5/2004 | Baczkowski |
| 6,874,500 | B2 | 4/2005 | Fukunaga et al. |
| 7,100,611 | B2 * | 9/2006 | Yu ............ 128/206.29 |
| 7,144,498 | B2 | 12/2006 | McCall et al. |
| 7,481,221 | B2 | 1/2009 | Kullik et al. |
| 7,513,252 | B2 | 4/2009 | Berg |
| 2006/0076013 | A1 | 4/2006 | Berg |
| 2006/0174889 | A1 | 8/2006 | Noble |
| 2008/0276941 | A1 | 11/2008 | Doty et al. |
| 2008/0295845 | A1 | 12/2008 | Nash |
| 2010/0122704 | A1 | 5/2010 | Moenning, Jr. |
| 2010/0122705 | A1 | 5/2010 | Moenning, Jr. |
| 2010/0122706 | A1 | 5/2010 | Moenning, Jr. |

FOREIGN PATENT DOCUMENTS

| | | |
|---|---|---|
| WO | 82/01999 A1 | 6/1982 |
| WO | 2007058574 A1 | 5/2007 |

OTHER PUBLICATIONS

Summer et al., "Sevoflurane in Exhaled Air of Operating Room Personnel," 2003, 1070-1073, 97, Anesthesia & Analgesia, Austria.

Sessler, et al., "Exposure of Postoperative Nurses to Exhaled Anesthetic Gases," 1998, 1083-1088, 87, Anesthesia & Analgesia.

Jiang, et al., "The Principle of Upper Airway Unidirectional Flow Facilitates Breathing in Humans," 2008, 854-858, 105, Journal of Applied Physiology.

"Waste Anesthetic Gases—Occupational Hazards in Hospitals," National Institute for Occupational Safety and Heatlh, Sep. 2007, DHHS (NIOSH) Publication No. 2007-151.

"Class II Special Controls Guidance Document: Filtering Facepiece Respirator for Use by the General Public in Public Health Medical Emergencies," Jul. 3, 2007, Center for Devices and Radiological Health—Guidance for Industry and FDA Staff.

Badgwell, J. Michael, "An Evaluation of Air Safety Source-Control Technology for the Post Anesthesia Care Unit," Journal of PeriAnesthesia Nursing, Aug. 1996, 207-222, 4.

Wharton, David F., "ASPAN's Environmental Health Task Force: Guarding the Health of Our Members," Journal of PeriAnesthesia Nurising, Aug. 2996, 202-203, 4.

"American Society of PeriAnesthesia Nurses—A Position Statement on Air Safety in the PeriAnesthesia Environment," Journal of PeriAnesthesia Nursing, Aug. 1996, 204-205, 4.

Ginsburg, William H., "Legal Issues in the Post Anesthesia Care Unit," Journal of PeriAnesthesia Nursing, Aug. 1996, 267-272, 4.

Definition of "evenlop", http://dictionary.reference.com/browse/envelop, accessed on Feb. 23, 2012, 1 page.

Supplemental European Search Report for European Patent Application No. 09828092.8-1662 / 2367589 PCT/US2009/064713, dated Jun. 25, 2014, 9 pages.

First Patent Examination Report, Australian Patent Application No. 2009316776, dated Dec. 1, 2014, 4 pages.

English translation of Japanese Office Action—Notification of Reasons for Rejection, Japanese Patent Application No. 2011-537546, dated Nov. 5, 2013, 2 pages.

First Examination Report issued by the New Zealand Patent Office for New Zealand Patent Application No. 592978, dated May 15, 2012, 3 pages.

Second Examination Report issued by the New Zealand Patent Office for New Zealand Patent Application No. 592978, dated Aug. 2, 2013, 2 pages.

Third Examination Report issued by the New Zealand Patent Office for New Zealand Patent Application No. 592978, dated Nov. 13, 2013, 2 pages.

* cited by examiner

COMBINATION ANESTHESIA AND SCAVENGER SURGICAL MASK

CLAIM OF PRIORITY

This application is a continuation of co-pending U.S. patent application Ser. No. 12/540,082, which is entitled "Combination Anesthesia and Scavenger Surgical Mask" and was filed on Aug. 12, 2009 by John E. Moenning, Jr., which is a continuation-in-part of U.S. patent application Ser. No. 12/273,748 (now U.S. Pat. No. 8,291,905), which is entitled "Combination Anesthesia and Scavenger Mask" and was filed on Nov. 19, 2008 by John E. Moenning, Jr. The entirety of both of the above-noted applications is hereby incorporated by reference.

CROSS REFERENCE TO RELATED APPLICATION

Cross reference is also made to U.S. patent application Ser. No. 12/540,085 (now U.S. Pat. No. 8,479,737), which is entitled "Combination Anesthesia and Scavenger Mask" and was filed on Aug. 12, 2009 by John E. Moenning, Jr., and the entirety of which is hereby incorporated by reference in its entirety.

TECHNICAL FIELD

The present disclosure relates generally to surgical masks, and more particularly to surgical masks used in the administration and scavenging of anesthesia gases.

BACKGROUND

Anesthesia gases are used on patients during surgical procedures. The administration of anesthesia gases to a patient involves the use of a mask placed over the nose and/or mouth of the patient. A gas administration circuit pumps the anesthesia gases into the mask for the patient to inhale through the nose and/or mouth.

SUMMARY

According to one aspect, there is provided a surgical mask having a nasal mask nested within an oral mask. Medical gases such as anesthesia gases and recovery gases are administered to a patient through the nasal mask. Gases exhaled by the patient are captured by the oral mask and exhausted to a scavenger circuit.

According to another aspect, a surgical mask assembly for administering and scavenging medical gases includes an outer mask having a first gas port configured to be coupled to a negative pressure source, and an inner mask secured to, and enveloped by, the outer mask. The inner mask has a second gas port that is configured to be coupled to a positive pressure source.

The outer mask may include a shell which defines a chamber with a rear-facing opening defined by a rim, along with a flexible seal secured to the rim.

The inner mask may be located in the chamber of the shell of the outer mask.

The inner mask may include a shell which defines a chamber with a rear-facing opening defined by a rim, and along with a flexible seal secured to the rim. The shell of the inner mask may be located in the chamber of the shell of the outer mask. In some embodiments, both the shell and the flexible seal of the inner mask may be located in the chamber of the shell of the outer mask.

The flexible seal of the inner mask seals the chamber of the inner mask from the chamber of the outer mask when the surgical mask assembly is positioned on the face of a patient.

The flexible seal of the outer mask envelops a patient's nose and mouth when the surgical mask assembly is positioned on the face of the patient, whereas the flexible seal of the inner mask envelops the patient's nose when the surgical mask assembly is positioned on the face of the patient.

The inner mask may be removable from the outer mask. In such embodiments, the outer mask may have an aperture defined therein, with the inner mask having a hollow tube extending outwardly therefrom. The hollow tube may be press fit into the aperture. The hollow tube may open into the chamber of the inner mask.

According to another aspect, a surgical mask assembly for administering and scavenging medical gases includes an oral mask and a nasal mask. The oral mask has a shell which defines a chamber with a rear-facing opening defined by a rim, a flexible seal secured to the rim, and a gas port. The flexible seal of the oral mask envelops a patient's nose and mouth when the surgical mask assembly is positioned on the face of the patient. The nasal mask includes a shell which defines a chamber with a rear-facing opening defined by a rim, a flexible seal secured to the rim, and a gas port. The flexible seal of the nasal mask envelops the patient's nose when the surgical mask assembly is positioned on the face of the patient.

The nasal mask may be located in the chamber of the shell of the oral mask.

The shell of the nasal mask may be located in the chamber of the shell of the oral mask. In some embodiments, both the shell and the flexible seal of the nasal mask are located in the chamber of the shell of the oral mask.

The flexible seal of the nasal mask seals the chamber of the nasal mask from the chamber of the oral mask when the surgical mask assembly is positioned on the face of a patient.

The nasal mask may be removable from the oral mask. In such embodiments, the shell of the oral mask may have an aperture defined therein, with the nasal mask having a hollow tube extending outwardly from the shell nasal mask. The hollow tube may open into the chamber of the nasal mask. The hollow tube may be press fit into the aperture defined in the shell of the oral mask.

According to another aspect, a method of administering medical gases to a patient during and subsequent to a medical procedure includes first coupling an oral mask to a source of anesthesia gas and supplying anesthesia gas to the patient via the oral mask. Then the oral mask may be decoupled from the source of anesthesia gas and coupled to a negative pressure source. A nasal mask may then be secured to the oral mask. The nasal mask is coupled to a source of post-operative recovery gas. The post-operative gas is supplied to the patient via the nasal mask and gas exhaled by the patient is evacuated via the oral mask.

The oral mask may be secured to the source of anesthesia gas during the medical procedure, and decoupled from source of anesthesia gas at completion of the medical procedure. The oral mask is coupled to the negative pressure source at completion of the medical procedure.

The post-operative recovery gas may be oxygen with such oxygen being supplied to the nasal mask to be inhaled through the patient's nose. The gases exhaled by the patient are evacuated via the oral mask.

BRIEF DESCRIPTION OF THE DRAWINGS

The detailed description particularly refers to the following figures, in which.

DETAILED DESCRIPTION OF THE DRAWINGS

Figure 1:
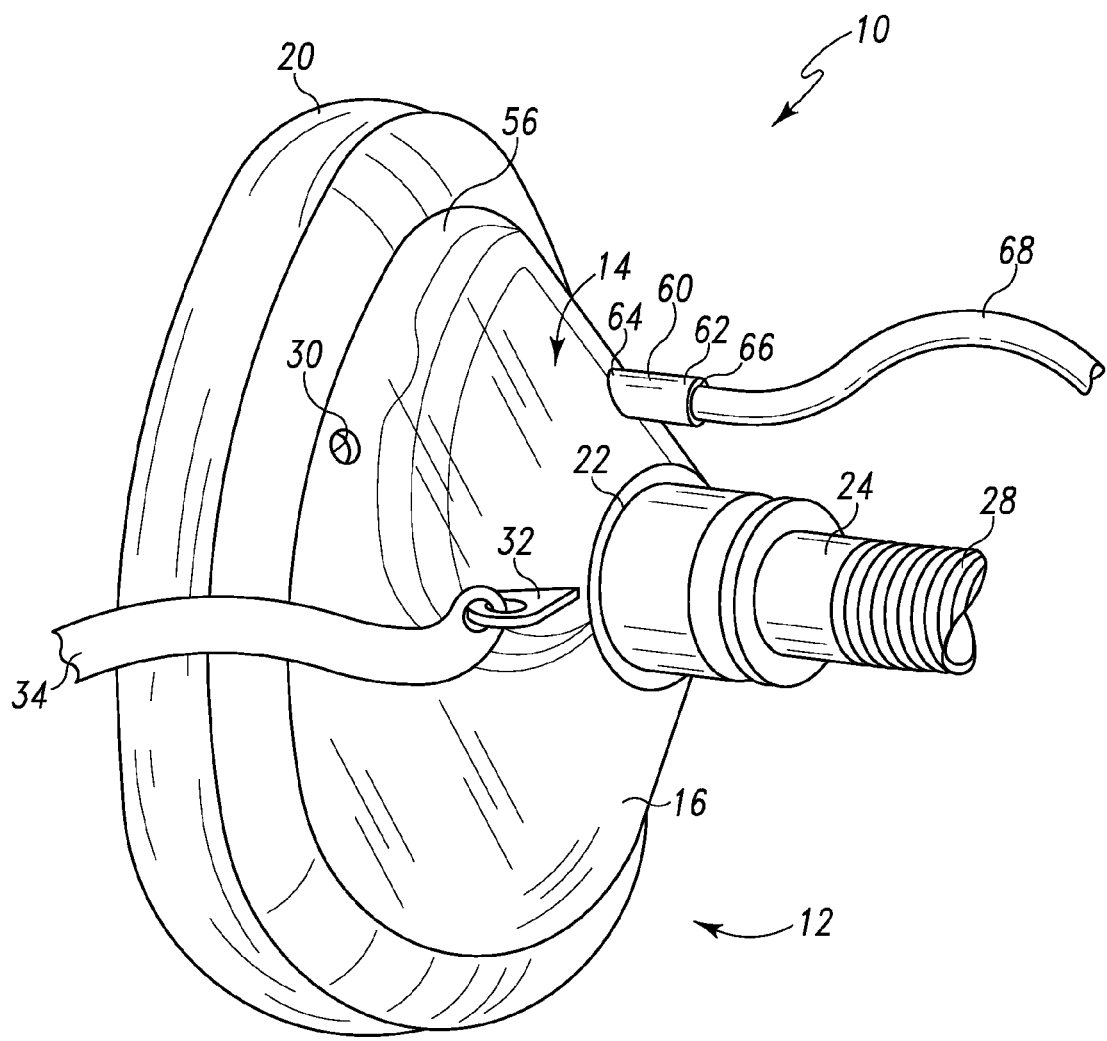
FIG. 1 is a perspective view of one embodiment of a surgical mask.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 2:
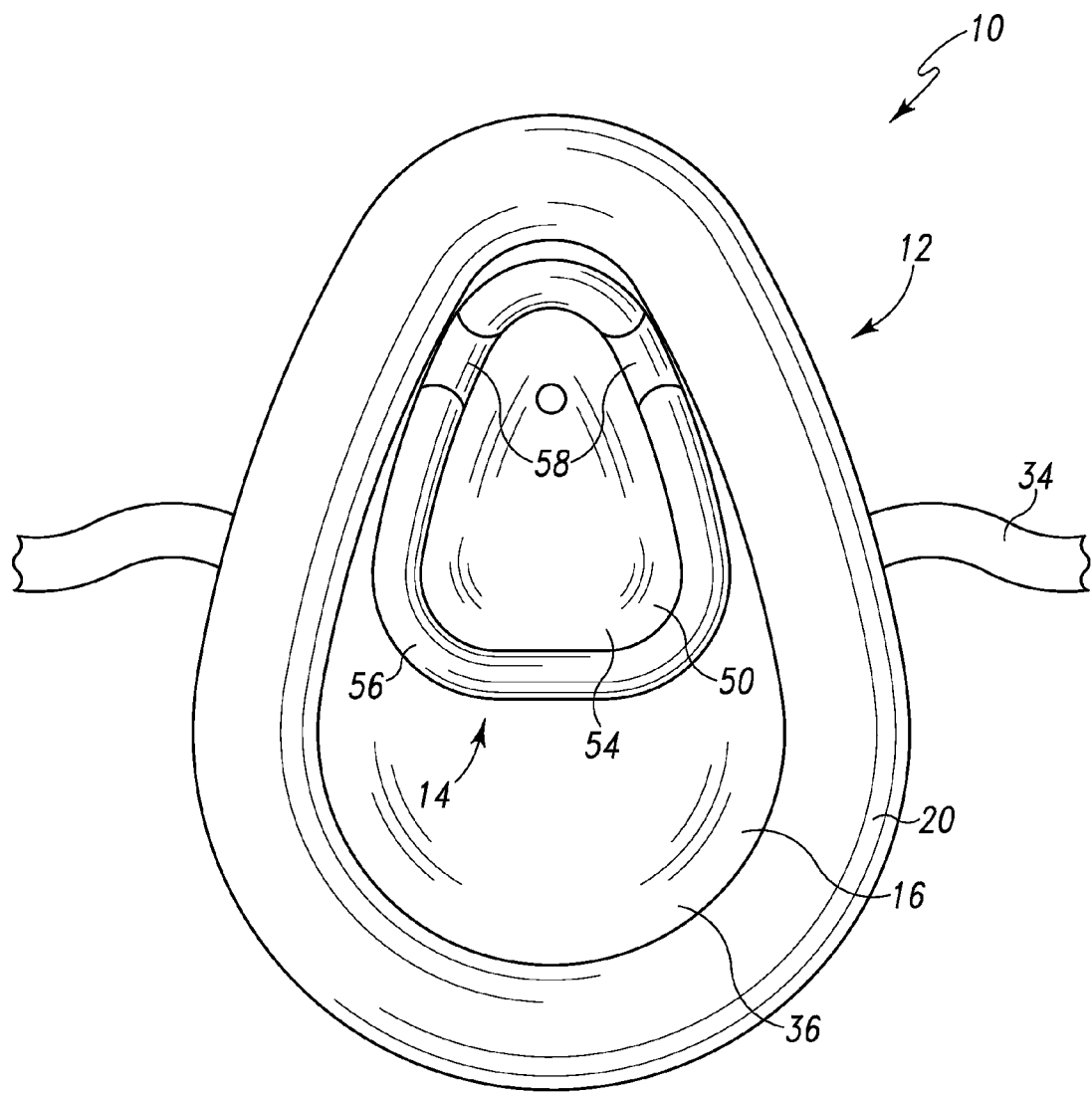
FIG. 2 is rear elevation view of the surgical mask of FIG. 1.
Figure 3:
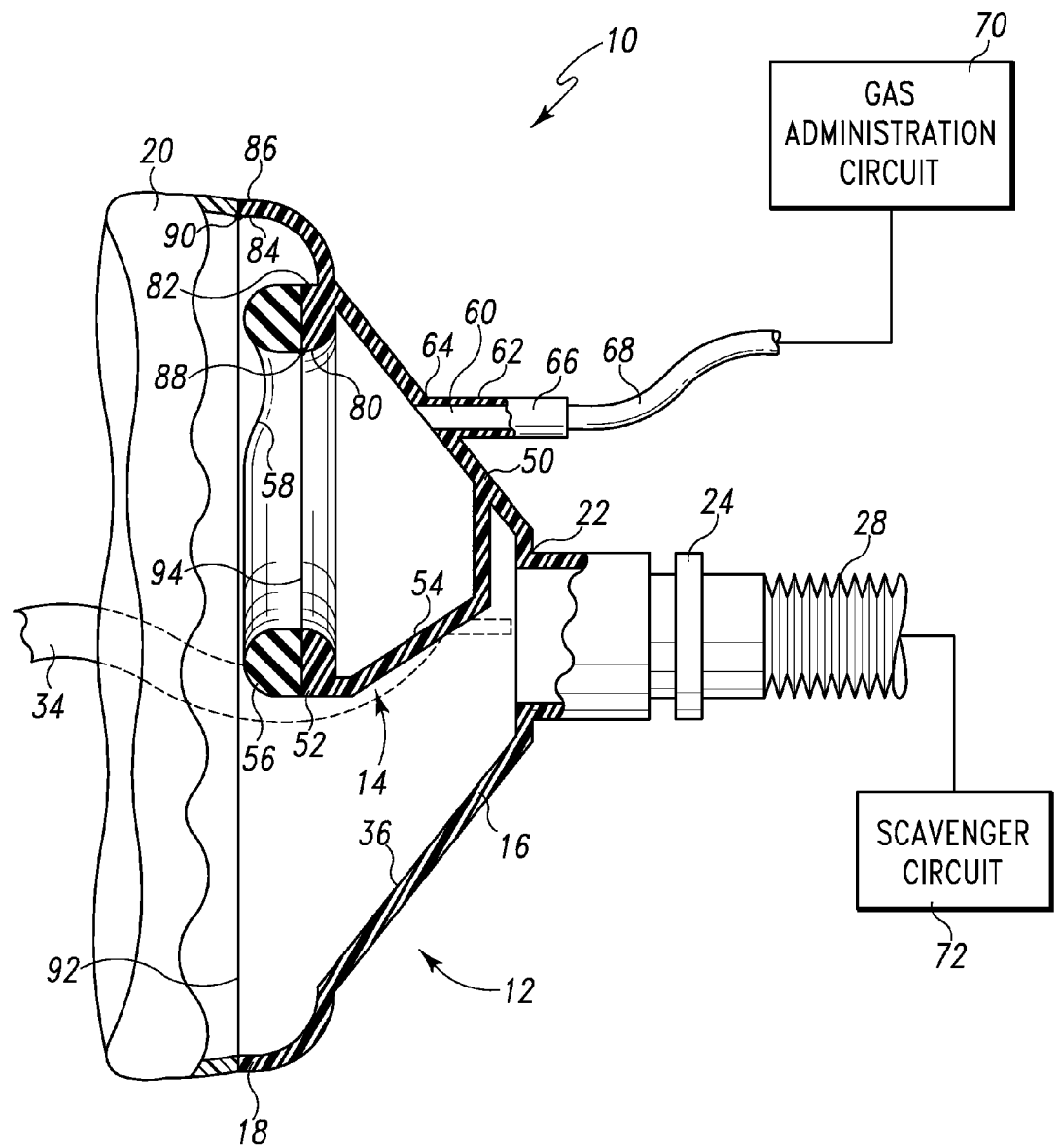
FIG. 3 is a cross-sectional view of the surgical mask of FIG. 1.

Referring to FIGS. 1-3, there is shown an illustrative embodiment of a combined anesthesia and scavenger surgical mask assembly 10 (hereinafter, simply, "surgical mask 10"). As will be discussed herein in greater detail, the surgical mask 10 may be used to deliver anesthesia or other medical gases to be inhaled by a patient. The surgical mask 10 also functions to scavenge the gases exhaled by the patient.

In the illustrative embodiment described herein, the surgical mask 10 includes an oral mask 12 having a nasal mask 14 nested therein. The oral mask 12 includes rigid or semi-rigid plastic shell 16. As best seen in FIG. 3, the shell 16 defines a hollow chamber 36 having a rear-facing opening defined by a rim 18. As can be seen in FIG. 2, the rear-facing opening of the shell 16 is generally pear-shaped when viewed from the rear of the mask. A pillow-type seal 20 is secured to the rim 18 of the shell 16. In the illustrative embodiment described herein, the seal 20 is embodied as a soft, flexible, air-filled bladder, although other types of seals may also be used. The seal 20 deforms to correspond with the contour of a patient's face when the doctor places the surgical mask 10 over the patient's nose and mouth. When the surgical mask 10 is positioned on the patient's face, the seal 20 envelops the area around the patient's nose and mouth in such a way as to create a seal between the oral mask 12 and the patient's face. In such a way, the patient's nose and mouth are sealed within the chamber 36.

A gas port 22 is defined in the shell 16 of the oral mask 12. The gas port 22 includes a hollow tube 24 that extends outwardly from the oral chamber 36. The hollow tube 24 has a proximal end that opens into the oral chamber 36. A threaded distal end 28 of the hollow tube 24 may be coupled (e.g., screwed) to a hose or other type of fluid line of a scavenger circuit 72 (see FIG. 3). As such, the chamber 36 of the oral mask 12 may be exposed to the negative fluid pressure generated by the scavenger circuit 72. In other words, when the threaded distal end 28 of the hollow tube 24 is coupled to the scavenger circuit 72, a vacuum pump (not shown) associated with the scavenger circuit 72 may be used to evacuate the gases exhaled by the patient into the oral mask 12. Although the distal end 28 of the hollow tube 24 is herein described as being threaded, it should be appreciated that other configurations may also be used to couple the oral mask 12 to the scavenger circuit.

The oral mask 12 also includes a number of holes 30 extending through the shell 16. The holes 30 allow for minor venting of the chamber 36 of the oral mask 12 when it is subjected to negative fluid pressure from the scavenger circuit 72. This prevents the oral mask 12 from uncomfortably locking onto the patient's face due to the suction generated by the scavenger circuit 72. The negative pressure in the chamber 36 of the oral mask 12 prevents exhaled gases from escaping through the holes 30.

One of a pair of strap mounts 32 is formed in the shell 16 of the oral mask 16 on either side of the port 22. An elastic strap 34 is secured to the strap mounts 32 and may be used to secure the surgical mask 10 to the patient's head.

As shown best in the cross section of FIG. 3, the oral mask 12 envelops the nasal mask 14. More specifically, the nasal mask 14 is located within the chamber 36 such that the chamber 36 envelops the nasal mask 14. When the surgical mask 10 is placed over the patient's face, the seal 20 also functions to seal the nasal mask 14 within the chamber 36.

Like the oral mask 12, the nasal mask 14 includes rigid or semi-rigid plastic shell 50. As best seen in FIG. 3, the shell 50 defines a hollow chamber 54 having a rear-facing opening defined by a rim 52. As can be seen in FIG. 2, the rear-facing opening of the shell 50 is generally pear-shaped when viewed from the rear of the mask. A flexible seal 56 is secured to the rim 52 of the shell 50. In the illustrative embodiment described herein, the seal 56 is embodied as a soft, flexible sealing ring, although other types of seals may also be used. The seal 56 corresponds with the contour of a patient's nose and the area of the face surrounding the nose when the doctor places the surgical mask 10 over the patient's nose and mouth.

A gas port 60 is defined in the shell 50 of the nasal mask 14. Although only one gas port 60 is shown in the illustrative embodiment described herein, it should be appreciated that any number of gas ports may be used. Moreover, the gas port 60 (or ports) may be located at various locations in the shell 50 to fit the needs of a given design. The gas port 60 includes a hollow tube 62 that extends outwardly from the nasal chamber 54. The hollow tube 62 has a proximal end 64 that opens into the nasal chamber 54. A distal end 66 of the hollow tube 62 may be coupled to a hose 68 or other type of fluid line of a medical gas administration circuit 70 (see FIG. 3). As such, the chamber 54 of the nasal mask 14 may be exposed to the medical gases (e.g., anesthesia gases or oxygen) supplied by the gas administration circuit 72. In other words, when the distal end 66 of the hollow tube 62 is coupled to the gas administration circuit 70, a supply pump (not shown) or pressurized tank (not shown) associated with the gas administration circuit 70 may be used to supply medical gases under positive pressure to the chamber 54 of the nasal mask 14 where such gases are then inhaled by the patient through the patient's nose. Although the distal end 66 of the hollow tube 62 is herein described as being slip fit onto the hose of the gas administration circuit 70, it should be appreciated that other configurations may also be used to couple the nasal mask 14 to the gas administration circuit.

The flexible seal 56 of the nasal mask 14 seals the chamber 54 of the nasal mask from the chamber 36 of the oral mask 12. In particular, when the surgical mask 10 is placed on the face of a patient, the flexible seal 56 seals to the patient's nose and the area of the face surrounding the nose thereby fluidly isolating the chamber 54 of the nasal mask from the chamber 36 of the oral mask 12. In such a way, medical gases (e.g., anesthesia gases or recovery oxygen) supplied by the gas administration circuit 72 can accumulate within the chamber 54 of the nasal mask 14 to be inhaled by the patient without being evacuated by the scavenger circuit 72 through the oral mask 12.

As shown in FIGS. 2 and 3, a pair of curved indentations 58 are formed in the rear edge of the flexible seal 56 near the portion of the seal 56 that engages the bridge of the patient's nose. The curved indentations 58 provide for a minor amount of selective fluid communication between the chamber 54 of the nasal mask 14 and the chamber 36 of the oral mask 12. Specifically, if the patient exhales heavily through his or her nostrils, the nasal mask is gently urged away from the bridge of the patient's nose. This allows the exhaled gases exiting through the patient's nostrils to pass from the chamber 54 of the nasal mask 14 into the chamber 36 of the oral mask 12 through the opening created by the space between the curved indentations 58 and the patient's nose.

In use, the surgical mask 10 may be positioned over the patient's nose and mouth to administer medical gases such as anesthesia gases to the patient. The strap 34 secures the mask 10 to the patient's head. The hollow tube 62 of the mask's gas port 60 is coupled to the hose 68 of the gas administration circuit 70. The hollow tube 24 of the gas port 22 is coupled to the hose of the scavenger circuit 72.

Once coupled in such a manner and strapped to the patient, anesthesia gases from the gas administration circuit 70 are allowed to flow into the chamber 54 of the nasal mask 14 via the mask's gas port 60. The patient inhales the anesthesia gases that accumulate in the chamber 54 through the nose. Meanwhile, the scavenger circuit 72 creates negative pressure in the chamber 36 of the oral mask 12. This negative pressure pulls gases exhaled from the patient's mouth out of the surgical mask 10 and into the scavenger circuit where they are processed and disposed.

The holes 30 formed in the shell of the oral mask 12 prevent the oral mask 12 from locking onto the patient's face due to the suction created by the negative pressure. Moreover, to the extent the patient exhales heavily out of his or her nostrils, the curved indentations 58 of the nasal mask 14 provide a fluid path that allows the exhaled gases from the patient's nostrils to pass from the nasal chamber 54 into the oral chamber 36 where they are scavenged along with the gases exhaled from the patient's mouth.

During post-operative recovery, the gas administration circuit 70 (or other gas source) may be operated to supply recovery gas, such as oxygen, to the patient via the hollow tube 62 of the mask's gas port 60. During such post-operative recovery, the patient will continue to outgas the anesthesia gases administered to the patient during the surgical procedure. As such, the scavenger circuit 72 continues to create negative pressure in the chamber 36 of the oral mask 12 thereby allowing the exhaled gases from the patient's mouth to be pulled from the surgical mask 10 during post-operative recovery.

Figure 4:
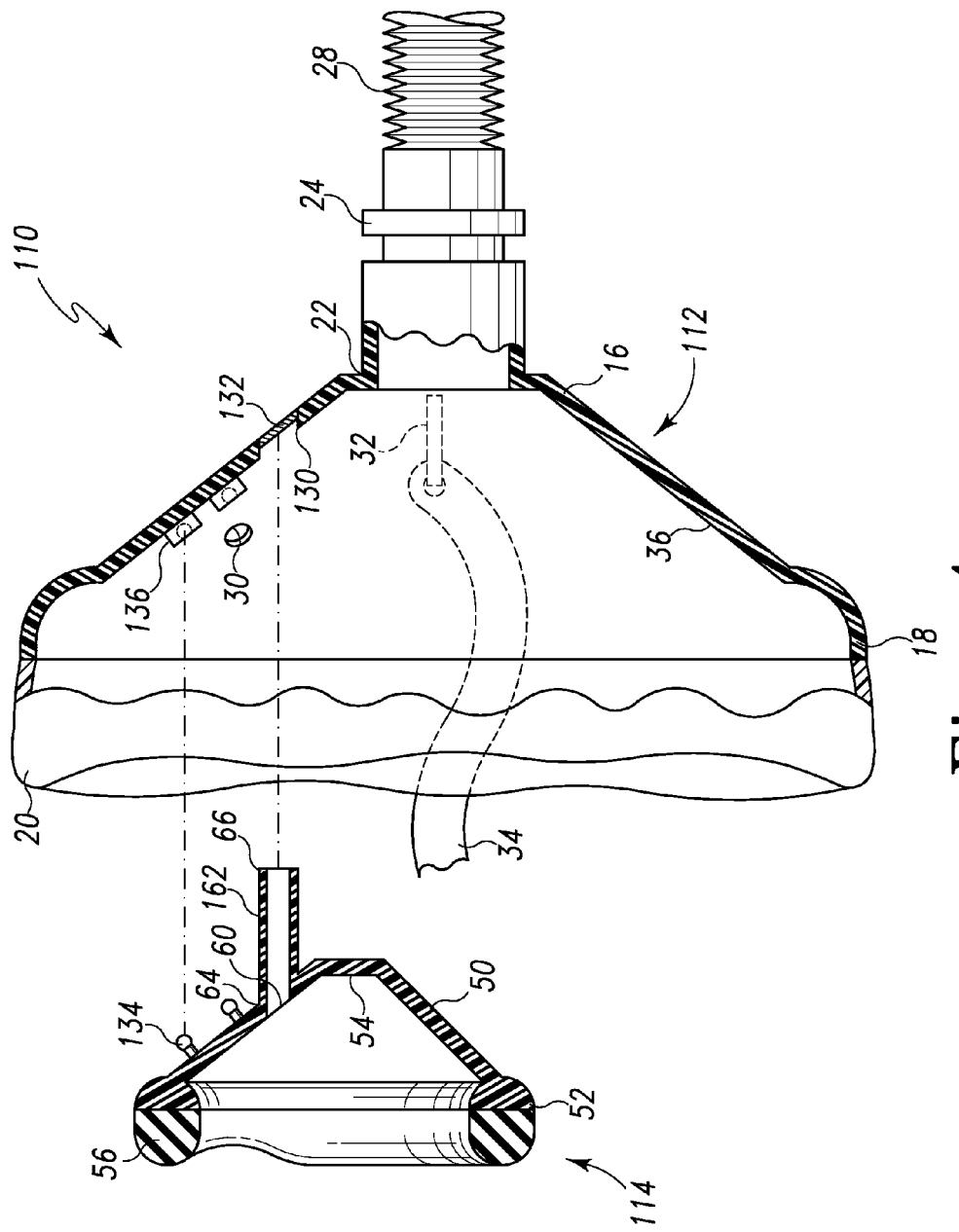
FIG. 4 is a cross-sectional view of another embodiment of a surgical mask.
Figure 5:
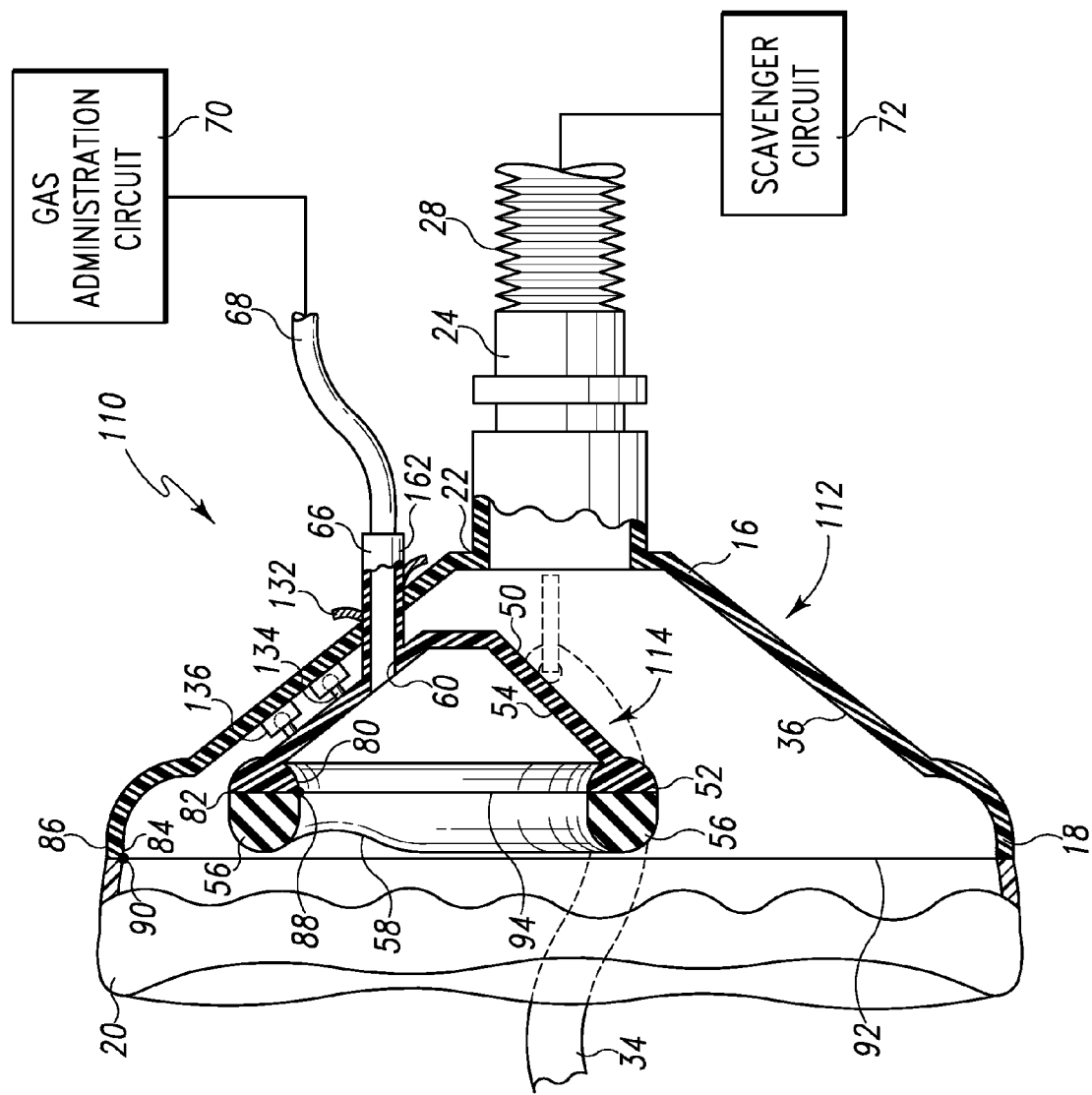
FIG. 5 is another cross-sectional view of the surgical mask of FIG. 4.

Referring now to FIGS. 4 and 5, a different embodiment of a surgical mask is shown (hereinafter referenced as a surgical mask 110). Some features of the embodiment illustrated in FIGS. 4 and 5 are substantially similar to those discussed above in reference to the embodiment of FIGS. 1-3. Such features are designated in FIGS. 4 and 5 with the same reference numbers as those used in FIGS. 1-3.

In the case of the surgical mask 110, the nasal mask 114 is removable from the oral mask 112. In such an arrangement, the oral mask 112 may be used as a conventional anesthesia mask when the nasal mask 114 is not attached. That is, the gas administration circuit 70 may be connected to the surgical mask 110 via the threaded distal end 28 of the oral mask 112. In this way, anesthesia gases may be delivered into the chamber 36 of the oral mask 112 where they are inhaled by the patient through the nose and/or the mouth.

The plastic shell 16 of the oral mask 112 has an aperture 130 formed therein. A cover 132 seals the aperture 130 thereby preventing gases within the chamber 36 from escaping through the aperture 130. The cover 132 may be made of a foil or plastic that can be torn, ripped, or pulled free from the oral mask 112. It should be appreciated that in other embodiments the cover 132 may be made of rubber or other suitable material.

A tapered hollow tube 162 extends outwardly from the nasal chamber 54 of the nasal mask 114. The hollow tube 162 has a proximal end 64 that opens into the nasal chamber 54. The distal end 66 of the hollow tube 162 may be coupled to the hose 68 or other type of fluid line of a medical gas administration circuit 70 (see FIG. 3). The outer diameter of the tapered hollow tube 162 increases from its distal end 66 in the direction toward its proximal end 64. Such an arrangement allows the tapered hollow tube 162 to be press fit (i.e., friction fit) into the aperture 130 formed in the plastic shell 16 of the oral mask 112 (see FIG. 5) thereby securing the nasal mask 114 to the oral mask 112.

The outer surface of the shell 50 of nasal mask 114 has a number of snap pins 134 extending outwardly therefrom. The inner surface of the shell 16 of the oral mask 112 has a corresponding number of catches or clips 136. The clips 136 of the oral mask 112 receive the snap pins 134 of the nasal mask 114 thereby securing the nasal mask 114 to the oral mask 112, as illustrated in FIG. 5. It should be appreciated that in other embodiments, other fasteners, joints, etc. may be used to secure the nasal mask 114 to the oral mask 112.

In use, the oral mask 112 may be used without the nasal mask 114 as a conventional anesthesia mask during surgery. In such an arrangement, the hollow tube 24 of the gas port 22 is coupled to a source of anesthesia gas (e.g., the gas administration circuit 70) so that anesthesia gases may flow into the chamber 36 of the oral mask 112 where they are inhaled by the patient through the nose and mouth. At the end of surgery, the oral mask 112 may then be converted to a scavenger mask for use in post-operative recovery in a similar manner to as described above in regard to the surgical mask 10. In particular, during post-operative recovery, the oral mask 112 may be disconnected from the gas administration circuit 70 (or other source of anesthesia gas) and connected to the scavenger circuit 72 by coupling the threaded distal end 28 of the hollow tube 24 to the scavenger circuit.

During such conversion of the oral mask 112, the nasal mask 114 may be installed to provide recovery gas (e.g., oxygen) to the patient. In particular, the nasal mask 114 may be advanced into the chamber 36 of the oral mask 112 so that the distal end 66 of its tapered hollow tube 162 is aligned with the aperture 130 formed in the plastic shell 16 of the oral mask 112. The distal end 66 of the hollow tube 162 is then urged into contact with the cover 132 thereby puncturing the cover 132. The hollow tube 162 is then press fit (i.e., friction fit) into the aperture 130 formed in the plastic shell 16 of the oral mask 112 (see FIG. 5). During such advancement of the nasal mask 114, the clips 136 of the oral mask 112 receive the snap pins 134 of the nasal mask 114. The combination of the press-fit connection of the tapered hollow tube 162 and the snap pins 134 secures the nasal mask 114 to the oral mask 112.

Once the nasal mask 114 is secured to the oral mask 112, it is connected to the gas administration circuit 70 via the tapered hollow tube 162. In such a way, the surgical mask 110 then functions similarly to the surgical mask 10 of FIGS. 1-3. In particular, during post-operative recovery, the gas administration circuit 70 (or other gas source) may be operated to supply recovery gas, such as oxygen, to the patient via the hollow tube 162 of the mask's gas port 60. During such post-operative recovery, the patient will continue to outgas the anesthesia gases administered to the patient during the surgical procedure. As such, the scavenger circuit 72 continues to create negative pressure in the chamber 36 of the oral mask 112 thereby allowing the exhaled gases from the patient's mouth to be pulled from the surgical mask 110 during post-operative recovery.

Figure 6:
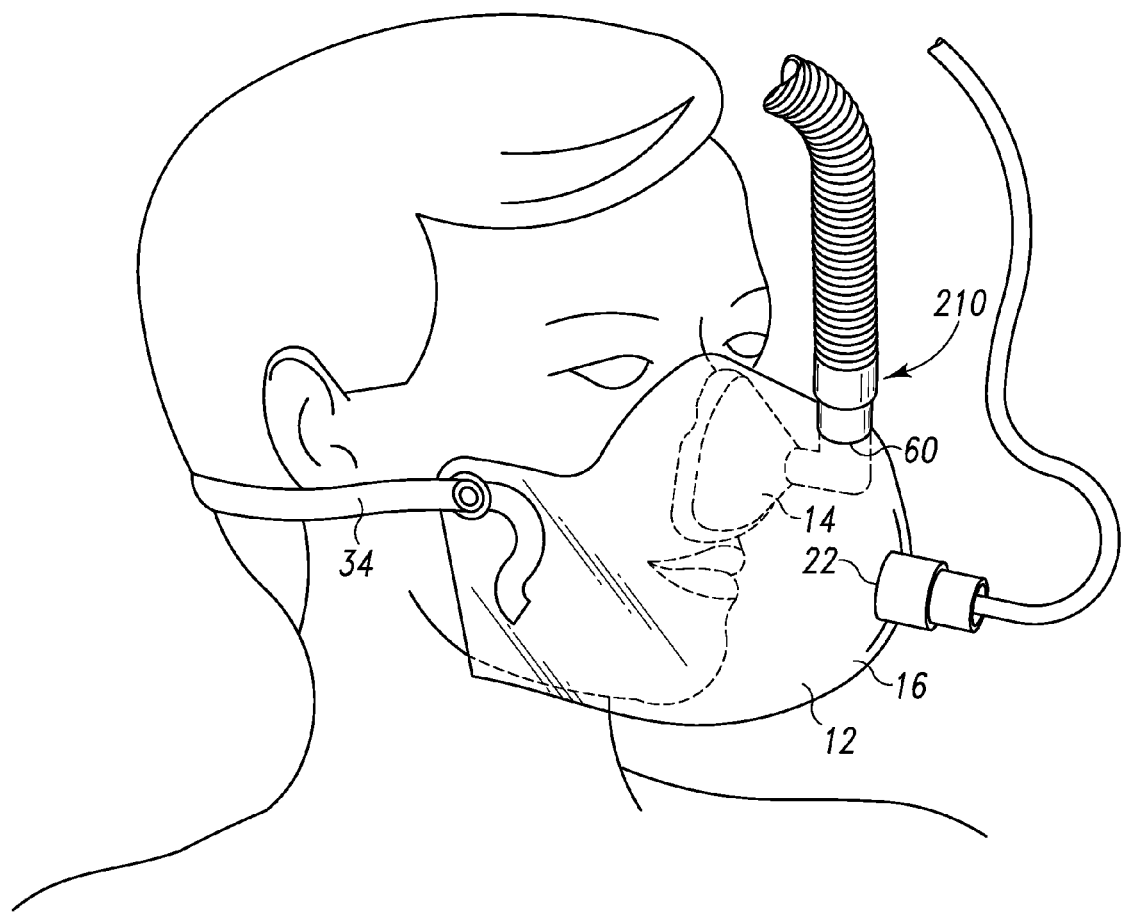
FIG. 6 is a perspective view of another embodiment of a surgical mask.
Figure 7:
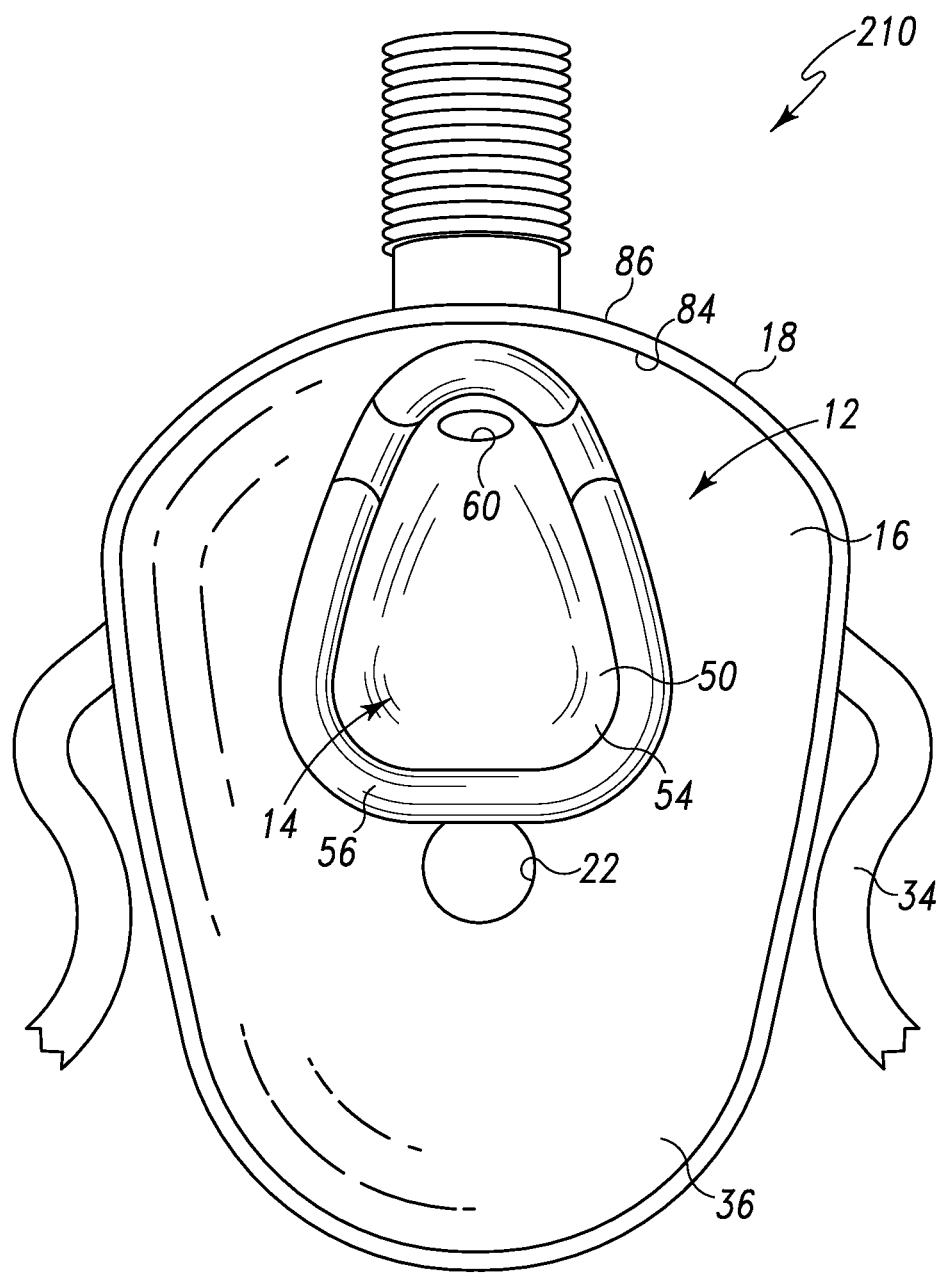
FIG. 7 is rear elevation view of the surgical mask of FIG. 6.
Figure 8:
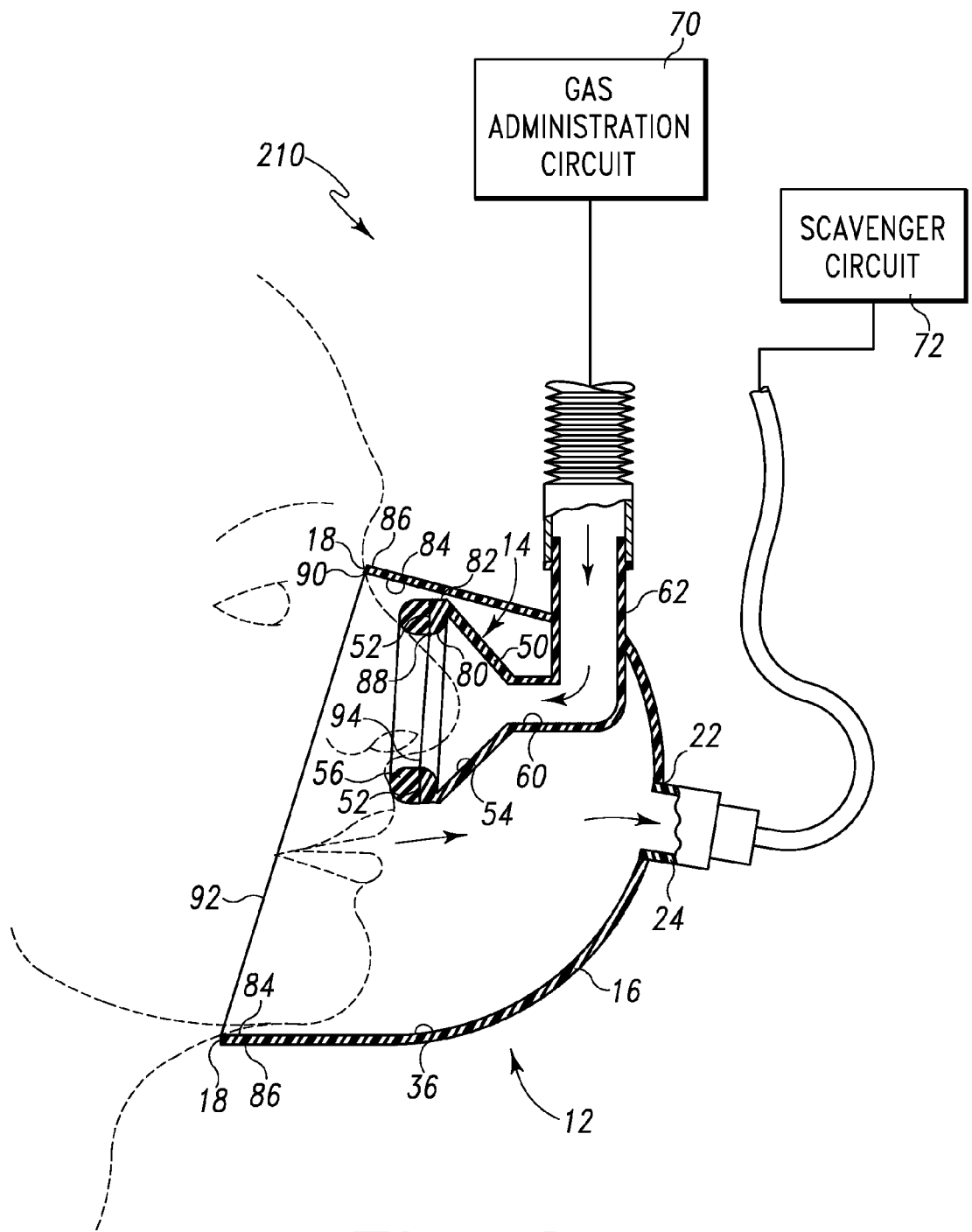
FIG. 8 is a cross-sectional view of the surgical mask of FIG. 6.

Referring now to FIGS. 6-8, a different embodiment of a surgical mask is shown (hereinafter referenced as a surgical mask 210). Some features of the embodiment illustrated in FIGS. 6-8 are substantially similar to those discussed above in reference to the embodiments of FIGS. 1-5. Such features are designated in FIGS. 6-8 with the same reference numbers as those used in FIGS. 1-5.

The surgical mask 210 is similar to the surgical mask 10 of FIGS. 1-3 with the exception of the design of the oral mask 12. In particular, the shell 16 of the oral mask 12 extends beyond the chin of the patient when the surgical mask 210 is positioned on the patient's face. In the illustrative embodiment described herein, the oral mask 12 of the surgical mask 210 does not have a seal secured to its rim 18. However, similar to the embodiments of FIGS. 1-5, the oral mask of a given design of the surgical masks described herein may include such a seal or be designed without it. In the case of a when the surgical mask 10, 110, 210 does not include such a seal on its oral mask, gases exhaled by the patient are prevented from leaking around the rim of the oral mask by the negative pressure in the chamber 36 of the oral mask 12 created by the vacuum pump of the scavenger circuit 72.

In a similar manner to the surgical masks 10, 110 of FIGS. 1-5, the nasal mask 14 of the surgical mask 210 is enveloped by the oral mask 12. More specifically, the nasal mask 14, including its rear-facing opening, is located within the chamber 36 of the oral mask 12 such that the chamber 36 envelops the nasal mask 14. As such, the rim 52 defining the rear-facing opening of the nasal mask 14 is positioned below and forward of the rim 18 defining the rear-facing opening of the oral mask. In regard to the surgical mask 210, this is demonstrated most readily in FIGS. 7 and 8 (and in FIGS. 3 and 5 in regard to the surgical masks 10, 110, respectively). Specifically, as viewed and described anatomically (in reference to use on a patient's face), the rim 52 of the shell 50 of the nasal mask 14 has an inner edge 80 and an outer edge 82, with the rim 18 of the shell 16 of the oral mask 12 having an inner edge 84 and an outer edge 86. The superior-most point 88 of the inner edge 80 of the rim 52 of the nasal mask 14 is positioned inferiorly and anteriorly relative to the superior-most point 90 of the inner edge 84 of the rim 18 of the oral mask 12. Such a configuration substantially, if not completely, eliminates the occurrences of gases exhaled through the nose escaping the surgical mask 10, 110, 210. This is in contrast to designs in which, for example, the superior edge of the nasal mask and the oral mask are formed on a common wall. In such designs, exhaled gases leaking around the bridge of the nose escape the surgical mask and are vented into the surrounding atmosphere.

Another way to characterize such a feature is in regard to the imaginary bounded planes formed by the rear-facing openings of the nasal mask 14 and the oral mask 12. In particular, the rear-facing opening defined by the rim 18 of the oral mask's shell 16 defines an imaginary bounded plane 92 (represented in the cross section views of FIGS. 3, 5, and 8 as a line). Likewise, the rear-facing opening defined by the rim 52 of the nasal mask's shell 50 defines an imaginary bounded plane 94 (represented in the cross section views of FIGS. 3, 5, and 8 as a line). As can be seen in FIGS. 3, 5, and 8, the bounded plane 94 defined by the nasal mask's rear-facing opening is positioned entirely within the chamber of the 36 of the oral mask 12. Said differently, the bounded plane 94 defined by the nasal mask's rear-facing opening is spaced apart from, and positioned anteriorly relative to, the bounded plane 92 defined by the oral mask's rear-facing opening.

In use, the surgical mask 210 performs similarly to the surgical masks 10, 110. Namely, the surgical mask 210 is positioned over the patient's nose and mouth to administer medical gases such as anesthesia gases to the patient. The strap 34 secures the mask 210 to the patient's head. The hollow tube 62 of the mask's gas port 60 is coupled to the hose 68 of the gas administration circuit 70. The hollow tube 24 of the gas port 22 is coupled to the hose of the scavenger circuit 72.

Once coupled in such a manner and strapped to the patient, anesthesia gases from the gas administration circuit 70 are allowed to flow into the chamber 54 of the nasal mask 14 via the mask's gas port 60. The patient inhales the anesthesia gases that accumulate in the chamber 54 through the nose. Meanwhile, the scavenger circuit 72 creates negative pressure in the chamber 36 of the oral mask 12. This negative pressure pulls gases exhaled from the patient's mouth out of the surgical mask 210 and into the scavenger circuit where they are processed and disposed.

During post-operative recovery, the gas administration circuit 70 (or other gas source) may be operated to supply recovery gas, such as oxygen, to the patient via the hollow tube 62 of the mask's gas port 60. During such post-operative recovery, the patient will continue to outgas the anesthesia gases administered to the patient during the surgical procedure. As such, the scavenger circuit 72 continues to create negative pressure in the chamber 36 of the oral mask 12 thereby allowing the exhaled gases from the patient's mouth to be pulled from the surgical mask 210 during post-operative recovery.

Figure 9:
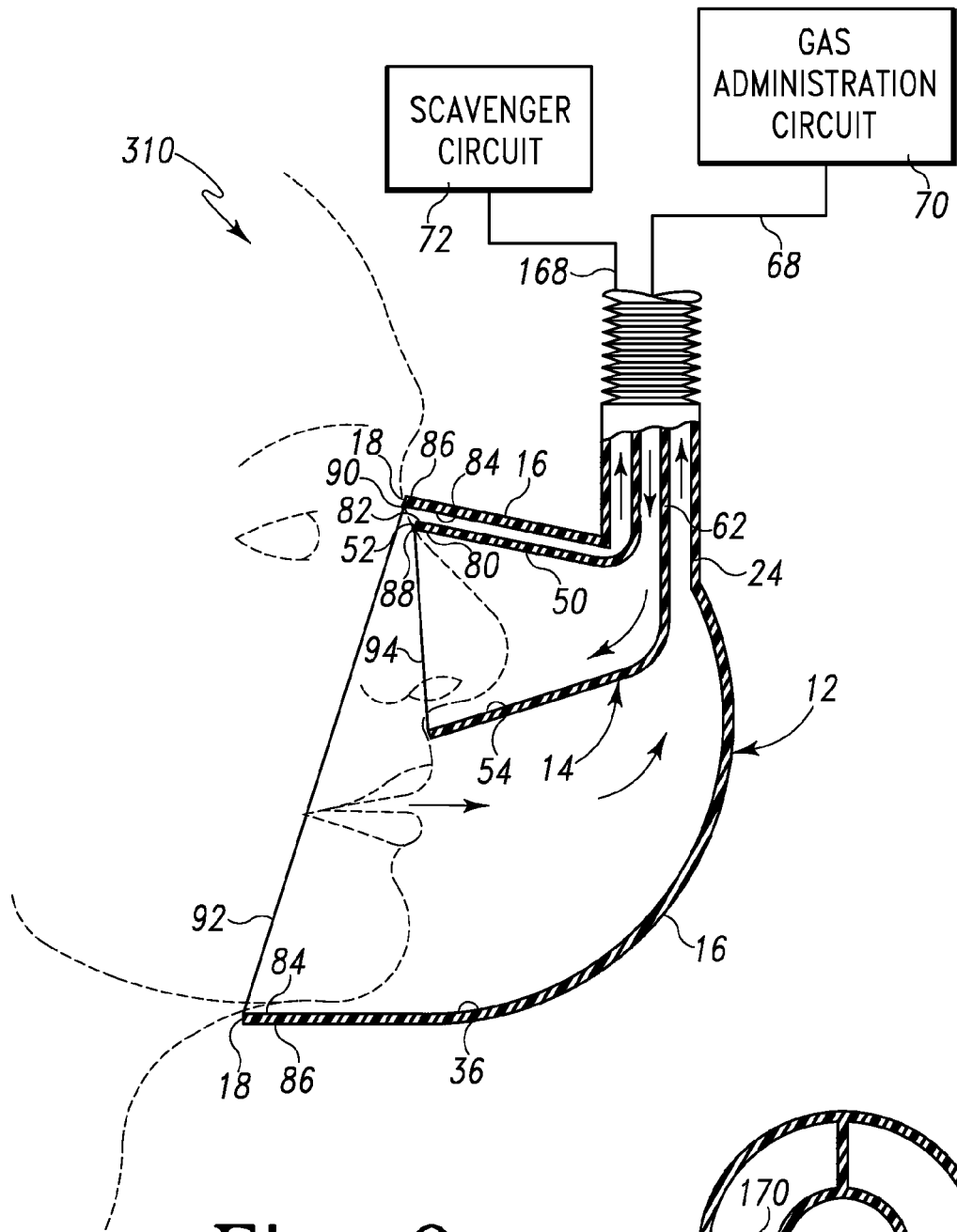
FIG. 9 is a cross-sectional view of another embodiment of a surgical mask.
Figure 10:
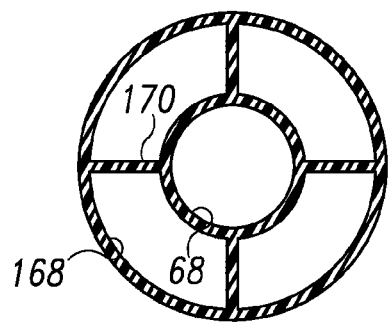
FIG. 10 is a cross-sectional view of a dual-lumen tube that may be used to couple the surgical mask of FIG. 9 to a gas administration circuit and a scavenger circuit.

Referring now to FIGS. 9 and 10, a different embodiment of a surgical mask is shown (hereinafter referenced as a surgical mask 310). Some features of the embodiment illustrated in FIGS. 9 and 10 are substantially similar to those discussed above in reference to the embodiments of FIGS. 1-8. Such features are designated in FIGS. 9 and 10 with the same reference numbers as those used in FIGS. 1-8.

The surgical mask 310 is similar to the surgical mask 210 of FIGS. 6-8 with the exception of the design of the nasal mask 14 and the gas ports (and associated tubing). In particular, in the illustrative embodiment described herein, the nasal mask 14 of the surgical mask 310 does not have a seal secured to its rim 52. However, similar to the embodiments of FIGS. 1-8, the oral mask of a given design of the surgical masks described herein may include the seal or be designed without it. In the case of a when the surgical mask 10, 110, 210, 310 does not include such a seal on its nasal mask, the bulk of the anesthesia and/or recovery gases delivered to the nasal mask 14 is inhaled by the patient with a small amount of such gases leaking around the rim of the nasal mask where they are scavenged via the negative pressure in the chamber 36 of the oral mask 12 created by the vacuum pump of the scavenger circuit 72. In other words, even though not sealed, the nasal mask 14 of the surgical mask 310 is used to create a local concentration of anesthesia and/or recovery gases that is sufficient to create the desired efficacy despite a portion of such gases being drawn directly into the scavenger circuit 72.

The gas port 22 of the oral mask 12 and the gas port 60 of the nasal mask 14 of the surgical mask 310 have been altered relative to the designs of FIGS. 1-8 to accommodate the use of a dual-lumen tubing design. In particular, the tubes connecting the surgical mask 310 to the gas administration circuit 70 and the scavenger circuit 72 are embodied as a dual-lumen tube. As such, the gas line 68 coupled to the gas administration circuit 70 extends through and is positioned within the gas line 168 coupled to the scavenger circuit 72. As can be seen in FIG. 10, a number of sidewalls 170 extend between the outer gas line 168 and the inner gas line 68 of the dual-lumen tube to maintain its structure. The use of the dual-lumen tube allows a single tube to be coupled to the surgical mask thereby facilitating its use. To facilitate the use of such a dual-lumen tube, the hollow tube 62 of the nasal mask's gas port 60 is positioned within the bore of the hollow tube 24 of the oral mask's gas port 22.

Figure 11:
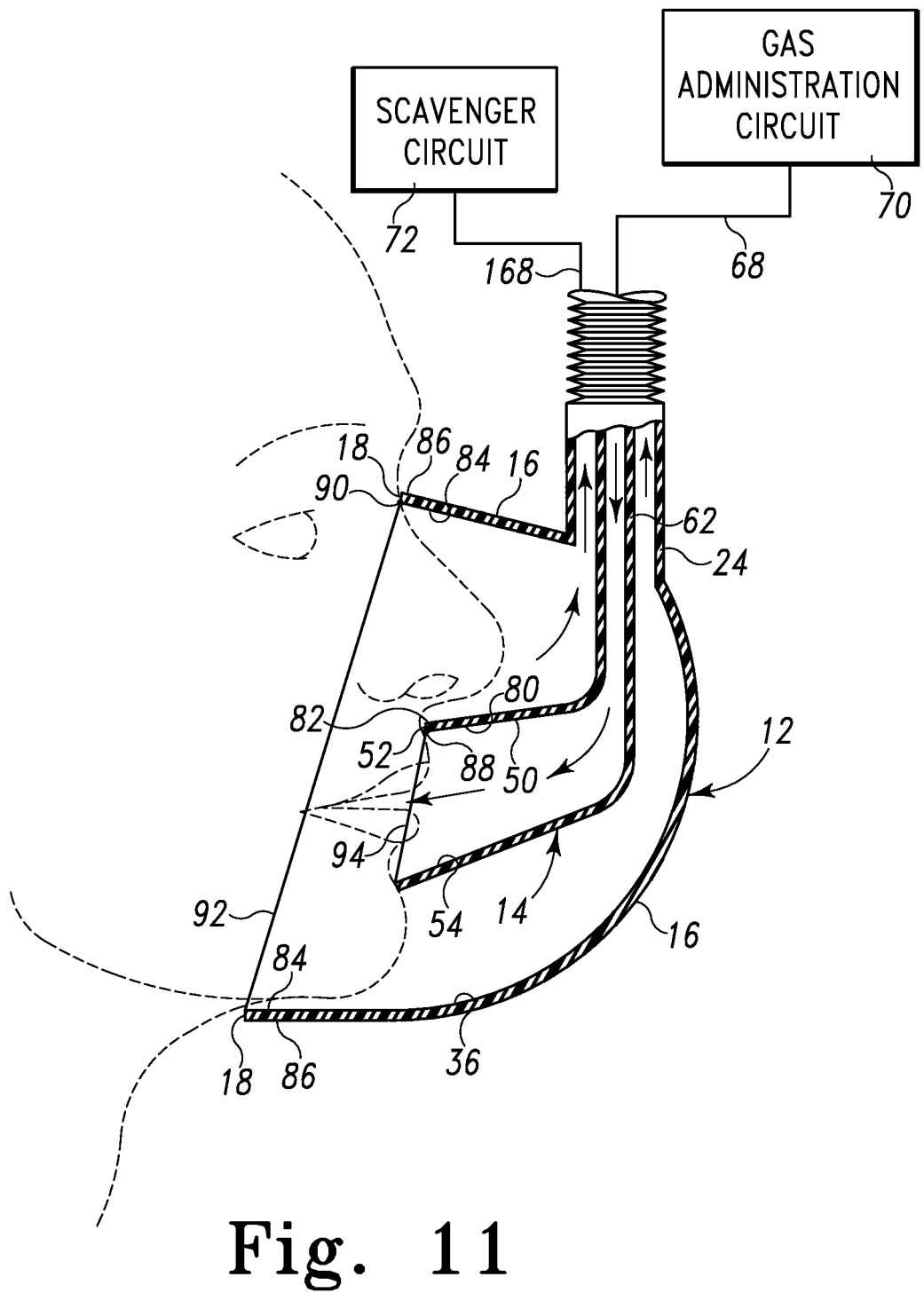
FIG. 11 is a cross-sectional view of another embodiment of a surgical mask.

Referring now to FIG. 11, a different embodiment of a surgical mask is shown (hereinafter referenced as a surgical mask 410). Some features of the embodiment illustrated in FIG. 11 are substantially similar to those discussed above in reference to the embodiments of FIGS. 1-10. Such features are designated in FIG. 11 with the same reference numbers as those used in FIGS. 1-10.

The surgical mask 410 is similar to the surgical mask 310 of FIGS. 9 and 10 with the exception of the design of the inner mask 14. In particular, in the illustrative embodiment described herein, the inner mask 14 of the surgical mask 410 is positioned to deliver anesthesia and/or recovery gases to the patient's mouth instead of the patient's nose. Gases exhaled by the patient are captured and scavenged by the outer mask 12 in the manner herein described in regard to the surgical masks 10, 110, 210, 310. The surgical mask 410 finds particular use in surgical procedures related to the nose in which the nose is "packed" or otherwise rendered unusable for the inhalation of gas.

A further modification to any of the surgical masks 10, 110, 210, 310, 410 includes the use of a viral filter. Namely, the surgical masks 10, 110, 210, 310, 410 may be embodied to include one or more viral filters to prevent the spread of viruses or other biological organisms/contaminants from the surgical mask. For example, such a filter may be placed proximate to the gas port(s) of the surgical mask to prevent the spread of viruses or other biological organisms/contaminants to the tube(s) connecting the surgical mask to the gas administration circuit 70 and the scavenger circuit 72 thereby allowing such tube(s) to be reused. In the case of a dual-lumen tube, a single viral filter may be used to filter both lines.

Alternatively to incorporating such a filter into the design of the surgical mask, a filter "cartridge" or similar structure may be installed between the gas port(s) of the surgical mask and the tube(s) connecting the surgical mask to the gas administration circuit 70 and the scavenger circuit 72. In such a case, both the surgical mask and the cartridge(s) may be disposed after each use with the tube(s) connecting the surgical mask to the gas administration circuit 70 and the scavenger circuit 72 being reusable.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical mask assembly for administering and scavenging medical gases, comprising:
    an outer shell having a gas port configured to be coupled to a negative pressure source, the outer shell defining a chamber with a rear-facing opening defined by a rim, the rim having an inner edge and an outer edge, and
    an inner shell defining a chamber with a rear-facing opening defined by a rim, the rim having an inner edge and an outer edge, the inner shell having a second gas port that includes (i) a distal end configured to be coupled to a positive pressure source, and (ii) a proximal end that opens into the chamber of the inner shell for supplying gas from the positive pressure source to the chamber of the inner shell,
    wherein (i) a superior-most point of the inner edge of the rim of the inner shell is positioned inferiorly and anteriorly relative to a superior-most point of the inner edge of the rim of the outer shell, (ii) the inner shell is configured to deliver gas to the patient's nose, but not envelop the patient's mouth, when the surgical mask assembly is positioned on the face of the patient, and (iii) the outer shell is configured to envelope both the patient's nose and mouth when the surgical mask assembly is positioned on the face of the patient.

2. The surgical mask assembly of claim 1, wherein the entire inner shell is located in the chamber of the outer shell.

3. The surgical mask assembly of claim 1, further comprising a flexible seal secured to the rim of the inner shell, wherein the flexible seal is located in the chamber of the outer shell.

4. The surgical mask assembly of claim 1, wherein:
    the inner shell envelops the patient's nose when the surgical mask assembly is positioned on the face of the patient.

5. The surgical mask assembly of claim 1, further comprising:
    a flexible seal secured to the rim of the inner shell, and
    a flexible seal secured to the rim of the outer shell.

6. The surgical mask of claim 1, wherein:
the gas port of the inner shell comprises a first tube,
the gas port of the outer shell comprises a second tube, and
the first tube is positioned within the second tube.

7. A surgical mask assembly for administering and scavenging medical gases, comprising:
an outer shell having a gas port configured to be coupled to a negative pressure source, the outer shell defining a chamber with a rear-facing opening defined by a rim, the rear-facing opening defining an imaginary bounded plane, and
an inner shell defining a chamber with a rear-facing opening defined by a rim, the rear-facing opening defining an imaginary bounded plane, the inner shell having a second gas port that includes (i) a distal end configured to be coupled to a positive pressure source, and (ii) a proximal end that opens into the chamber of the inner shell for supplying gas from the positive pressure source to the chamber of the inner shell,
wherein (i) the imaginary bounded plane defined by the rear-facing opening of the inner shell is spaced apart from, and positioned anteriorly relative to, the imaginary bounded plane defined by the rear-facing opening of the outer shell, (ii) the inner shell is configured to deliver gas to the patient's nose, but not envelop the patient's mouth, when the surgical mask assembly is positioned on the face of the patient, and (iii) the outer shell is configured to envelope both the patient's nose and mouth when the surgical mask assembly is positioned on the face of the patient.

8. The surgical mask assembly of claim 7, wherein the entire inner shell is located in the chamber of the outer shell.

9. The surgical mask assembly of claim 7, further comprising a flexible seal secured to the rim of the inner shell, wherein the flexible seal is located in the chamber of the outer shell.

10. The surgical mask assembly of claim 7, wherein:
the inner shell envelops the patient's nose when the surgical mask assembly is positioned on the face of the patient.

11. The surgical mask assembly of claim 7, further comprising:
a flexible seal secured to the rim of the inner shell, and
a flexible seal secured to the rim of the outer shell.

12. The surgical mask of claim 7, wherein:
the gas port of the inner shell comprises a first tube,
the gas port of the outer shell comprises a second tube, and
the first tube is positioned within the second tube.

13. A surgical mask assembly for administering and scavenging medical gases, comprising:
an outer shell having a first gas port configured to be coupled to a negative pressure source, the outer shell defining a chamber with a rear-facing opening defined by a rim, and
an inner shell secured to the outer shell, the inner shell defining a chamber with a rear-facing opening defined by a rim and having a second gas port that includes (i) a distal end configured to be coupled to a positive pressure source, and (ii) a proximal end that opens into the chamber of the inner shell for supplying gas from the positive pressure source to the chamber of the inner shell, wherein (i) the rim of the inner shell is enveloped by the outer shell, (ii) the inner shell is configured to deliver gas to the patient's nose, but not envelop the patient's mouth, when the surgical mask assembly is positioned on the face of the patient, and (iii) the outer shell is configured to envelope both the patient's nose and mouth when the surgical mask assembly is positioned on the face of the patient.

14. The surgical mask assembly of claim 13, wherein the inner shell is located in the chamber of the outer shell.

15. The surgical mask assembly of claim 13, wherein:
a flexible seal secured to the rim of the inner shell, and
the flexible seal is located in the chamber of the outer shell.

16. The surgical mask assembly of claim 13, wherein the rim of the inner shell is located in the chamber of the outer shell.

17. The surgical mask assembly of claim 13, wherein:
the inner shell envelops the patient's nose when the surgical mask assembly is positioned on the face of the patient.

18. The surgical mask assembly of claim 13, wherein a flexible seal is secured to the rim of the inner shell.

19. The surgical mask assembly of claim 18, wherein a flexible seal is secured to the rim of the outer shell.

* * * * *